United States Patent [19]

Granger et al.

[11] Patent Number: 5,259,846
[45] Date of Patent: Nov. 9, 1993

[54] LOOP THREADED COMBINED SURGICAL NEEDLE-SUTURE DEVICE

[75] Inventors: Richard N. Granger, Huntington; George R. Proto, West Haven, both of Conn.

[73] Assignee: United States Surgical Corporation, Norwalk, Conn.

[21] Appl. No.: 638,195

[22] Filed: Jan. 7, 1991

[51] Int. Cl.⁵ .............................. A61B 17/00
[52] U.S. Cl. ..................... 606/224; 606/223
[58] Field of Search ............... 606/223–227, 606/

[56] References Cited

U.S. PATENT DOCUMENTS

| | | | |
|---|---|---|---|
| 386,723 | 7/1888 | Smith . | |
| 508,745 | 11/1893 | Paul . | |
| 879,758 | 2/1908 | Foster . | |
| 1,293,660 | 2/1919 | Armstrong . | |
| 1,665,216 | 4/1928 | Morton et al. . | |
| 1,960,117 | 5/1934 | Lydeard . | |
| 2,715,486 | 8/1955 | Marcoff-Moghadam et al. . | |
| 2,716,515 | 8/1955 | Moghadam . | |
| 2,865,375 | 12/1958 | Banks et al. . | |
| 2,983,898 | 5/1961 | Kalmar et al. . | |
| 3,233,800 | 2/1966 | Catania . | |
| 3,534,740 | 10/1970 | Thompson | 606/226 |
| 3,570,497 | 3/1971 | Lemole . | |
| 3,762,418 | 10/1973 | Wasson | 606/226 |
| 3,924,630 | 12/1975 | Walldorf | 606/226 |
| 4,060,885 | 12/1977 | Hoffman et al. . | |
| 4,072,041 | 2/1978 | Hoffman et al. | 606/226 |
| 4,133,339 | 1/1979 | Naslund . | |
| 4,182,341 | 1/1980 | Perri | 606/224 |
| 4,392,495 | 7/1983 | Bayers . | |
| 4,535,764 | 8/1985 | Ebert . | |
| 4,901,721 | 2/1990 | Hakki | 606/224 |
| 4,922,904 | 5/1990 | Uetake et al. | 606/226 |
| 4,932,962 | 6/1990 | Yoon et al. . | |
| 4,950,285 | 8/1990 | Wilk | 606/232 |
| 5,074,874 | 12/1991 | Yoon et al. | 606/224 |

FOREIGN PATENT DOCUMENTS

| | | |
|---|---|---|
| 0040187 | 11/1981 | European Pat. Off. . |
| 0426377 | 5/1991 | European Pat. Off. . |
| 0426378 | 5/1991 | European Pat. Off. . |
| 2356404 | 1/1978 | France . |
| 560599 | 8/1977 | U.S.S.R. ............... 606/224 |
| 820811 | 4/1981 | U.S.S.R. . |
| 780868 | 8/1957 | United Kingdom . |
| 1526222 | 9/1978 | United Kingdom . |

OTHER PUBLICATIONS

McCulloch, RJP, "Corneoscleral sutures" Arch Ophth. vol. 31: p. 262, 1944.

Primary Examiner—Stephen C. Pellegrino
Assistant Examiner—Gary Jackson
Attorney, Agent, or Firm—Thomas R. Bremer; Peter G. Dilworth; Rocco S. Barrese

[57] ABSTRACT

A loop threaded needle-suture device is disclosed wherein a surgical needle is provided with a pointed end and a drilled aperture extending axially of the butt end, and a length of flexible suture material is doubled upon itself to form a loop, both free ends of which are attached to the needle in the butt end aperture. The blunt end of the needle is deformed to form the aperture into an elliptical cross-section and the length of the loop is substantially greater than the length of the needle to facilitate insertion of the needle and suture material into tissue to be sutured, and looping the needle through the suture material prior to tieing the suture material. Thus, the loop functions as a double suture. A method of forming the unique loop threaded needle-suture is disclosed.

26 Claims, 2 Drawing Sheets

LOOP THREADED COMBINED SURGICAL NEEDLE-SUTURE DEVICE

BACKGROUND OF THE INVENTION

1. Field of the Invention

This invention relates to a combined surgical needle-suture device and more particularly to a drilled needle-suture device in which a suture, in the form of a looped thread, is attached to the needle.

2. Description of the Prior Art

For many years, surgeons have employed needle-suture combinations in which a suture or ligature is attached to the shank end of a needle. Such needle-suture combinations are provided for a wide variety of monofilament and multifilament braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations generally fall into three classes: eyed, with no suture attached; drilled end, i.e. with an aperture bored down the long axis of the needle and a suture secured in the bore; and channeled, i.e. with a U-shaped recess or channel with an end of the suture secured in the channel. Examples of drilled and channeled needles are provided by U.S. Pat. No. 3,534,740, while eyed needles are disclosed, for example, in U.S. Pat. Nos. 1,960,117 and 4,182,341. The last mentioned '341 patent incorporates a relatively short loop of polymer strand to form the eye of the needle.

More recently, it has become increasingly desirable to reduce the time required to suture a wound or opening and to tie the suture satisfactorily. While threading the suture has become improved somewhat, the last mentioned objective of quickly tieing the suture has not been significantly improved. The present invention incorporates a looped suture into a surgical needle to facilitate quick knotting and tieing as needed during critical surgical procedures.

SUMMARY OF THE INVENTION

It has now been found that an improved loop threaded needle-suture device can be provided by employing a drilled needle in place of a channeled needle wherein the butt end of the needle is provided with a looped flexible suture attached within a substantially elliptical shaped bore. The loop functions as the actual suture material.

The invention relates to a looped suture device which comprises a needle having a pointed end and a butt end, the butt end having an aperture extending generally axially thereof and having a cross-sectional dimension greater in a first direction than the cross-sectional dimension substantially perpendicular to the first direction, a loop formed from a suture material and having both free ends positioned within the aperture and attached to the needle. The looped suture device may include a curved surgical needle or a straight needle manufactured of any surgically acceptable metal alloy such as 400 series surgical stainless steel.

By "Aperture" is meant an opening surrounded on all sides by material forming the butt end of the needle, as compared to a channel which is open on one side. With a channeled needle it would be difficult to insert and retain both suture ends into the channel during the swaging process. Further, swaging the open ends of the channel without surface irregularities presents a separate and distinct difficulty.

The suture material includes such suture materials as polypropylene, silk, nylon, linen, cotton, polyester, stainless steel, natural materials such as catgut, and synthetic polymers having glycolic acid ester linkages subject to hydrolytic degradation to non-toxic, tissue compatible absorbable components, including polyglycolic acid. Monofilament and multifilament materials may be used.

Initially a needle is provided having an oversized drilled aperture in the butt end. The butt end is swaged to form the aperture into an elliptical shape. After inserting the two free ends of the looped flexible suture material into the aperture, the butt end of the pointed needle is inwardly swaged in at least one direction to provide inward force directed at the flexible suture material to attach the suture material to the needle. Alternatively, dies requiring a single hit may be utilized.

The flexible suture material loop is of sufficient length to facilitate looping the needle through the loop to tie the suture after passing the needle and a portion of the loop through the body tissue.

Although the examples set forth hereinbelow are directed to standard needle suture attachments, the invention is nevertheless applicable to removable needle attachments. The minimum acceptable forces required to separate a needle from a suture are set forth for various suture sizes in the United States Pharmacopeia ("USP"). For example, the USP prescribes minimum individual pull-out forces and minimum average pull-out forces as measured for various representative needle-suture combinations for both standard and removable needle/suture attachments. The minimum acceptable pull-out forces for both standard and removable needle-suture attachments set forth in the USP are hereby incorporated by reference. However, in practicing the present invention, the pull-out force for both standard and detachable sutures should be comparable to the stated pull out force for a single strand of the same size suture. Thus, the closure of the butt end of the needle with respect to the doubled or "end to end" suture portions positioned within the butt end of the needle as disclosed herein can be modified appropriately by persons skilled in the art to accomplish the same attachment (in Kgf) as with a single strand positioned in the needle butt end. Examples of the present invention are set forth hereinbelow for relatively large size suture strands having standard needle/suture attachments of about 2.10 (Kgf). For the size suture strand used, this attachment force is slightly greater than the average force set forth in the USP Examples. Accordingly, some variations of this force with the suture size listed are permissible within the scope of the invention.

The looped suture device includes a flexible suture loop of length sufficient to permit insertion of the needle into body tissue to be sutured and thereafter, reversing the direction of the needle and inserting it into the loop to facilitate tieing or knotting the suture prior to releasing the suture from the needle. Essentially, the provision of an elliptical opening at the butt end of the needle facilitates insertion and attachment of the loop of suture material to the needle aperture with the free ends of the suture material in adjacent engaged relation in the elliptical aperture. However, broadly any aperture having a major dimension and a lesser minor dimension transverse to the major dimension is contemplated. The loop is preferably at least 60 inches in total length, doubled to form a loop of 30 inches.

A method is disclosed for manufacturing a looped suture device which comprises taking a surgical needle having a pointed end and a butt end, the butt end having an aperture extending axially thereof and of predetermined length, providing a flexible suture material and looping the suture material such that the two free ends thereof are in adjacent engaged side-to-side relation. The method comprises deforming the butt end such that the aperture assumes a cross-sectional shape having a major dimension greater in length than a minor dimension substantially perpendicular to the major dimension. The aperture of the needle is dimensioned sufficient to receive a predetermined length of the free end portions of the flexible suture material while maintaining the free end portions in the end to end relation. According to the method at least one inwardly directed force is provided on the butt end of the needle to cause the needle material to become inwardly swaged sufficient to provide inward predetermined attachment force on the suture material. With standard needle suture dies requiring at least two hits, the second and subsequent inwardly directed forces are provided on the butt end of the needle in directions generally perpendicular to the provided force to thereby cause the needle material to become further swaged to provide predetermined attachment force on the flexible suture material.

Particular improved dies are disclosed in application Ser. No. 431,303, filed Nov. 3, 1989, now U.S. Pat. No. 5,046,350, and Ser. No. 431,306, filed Nov. 3, 1989, now U.S. Pat. No. 5,099,676, which are incorporated herein by reference. With such improved dies, a single hit may be used to attach the needle and the looped suture material.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
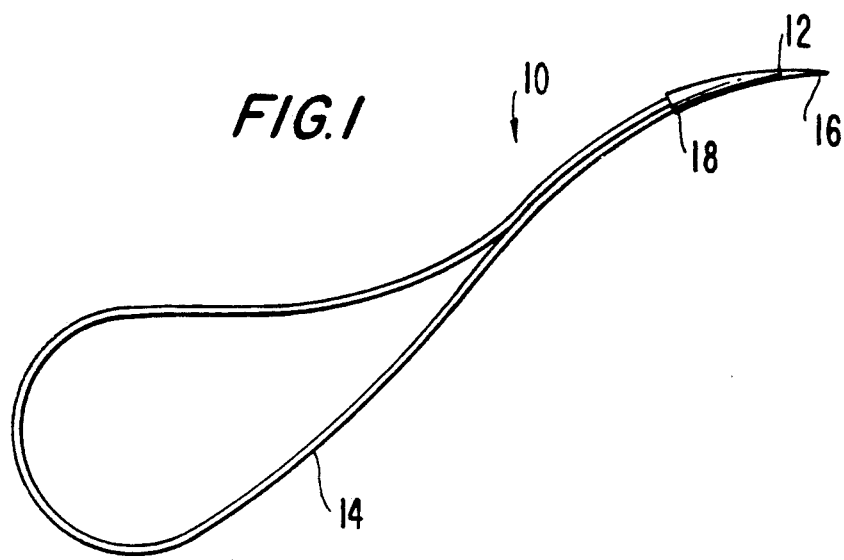
FIG. 1 is a perspective view of a looped suture device constructed according to the invention.

Referring initially to FIG. 1 the looped suture device 10 constructed according to the present invention is illustrated. The looped suture device is formed of surgical needle 12 attached to flexible suture material 14 as shown. The needle is preferably constructed of a suitable surgical steel such as surgical stainless steel and has pointed end 16 and butt end 18. Such materials as 300 and 400 series surgical stainless steel are contemplated. However, any suitable surgically approved metal alloy may be used. The actual suture is in the form of a loop.

Figure 2:
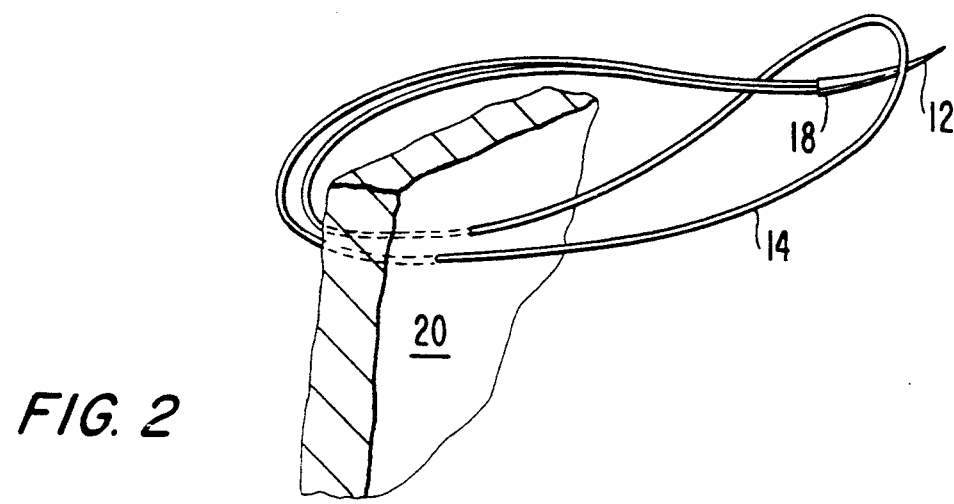
FIG. 2 is a perspective view of the looped suture device of FIG. 1 inserted into body tissue and looped upon itself.

Referring now to FIG. 2, a significant feature of the looped suture device is illustrated. The needle 12 is inserted into a portion of body tissue (illustrated schematically at 20). Thereafter, the suture device may be conveniently looped upon itself as shown, by inserting the pointed end of the needle into the looped suture material 14 and forming an appropriate tie or knot to secure the device with respect to the tissue. Tieing or knotting may not be required if the suture is being applied only for the purpose of restraining tissue during a surgical procedure.

Figure 3:
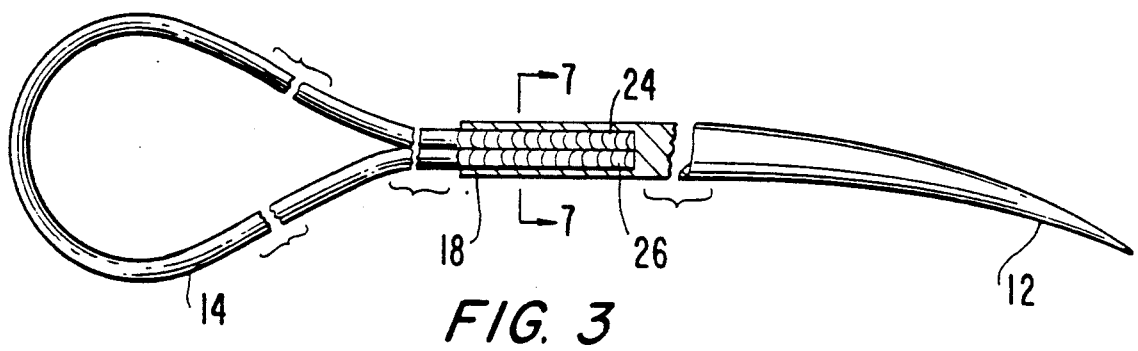
FIG. 3 is a plan view, partially in cross-section, and partially broken away, of the looped suture device shown in FIG. 1.

In FIG. 3, the looped flexible suture material 14 is illustrated with portions broken away, with both free ends 24, 26 positioned in adjacent end to end relation within an elongated elliptical aperture which extends axially of the butt end 18 of the needle. The needle is shown greatly enlarged in FIG. 3 for illustrative purposes. The cross-sectional view shown in FIG. 4 illustrates the attachment.

The present invention may be utilized in numerous applications including 1) starting a continuous stitch by tieing a knot with the flexible suture material; 2) restraining tissue temporarily during a surgical procedure; 3) inserting the suture device with the flexible portion partially into the tissue and tieing a knot. Clearly, other applications will readily come to the mind of a person skilled in the art.

Figure 4:
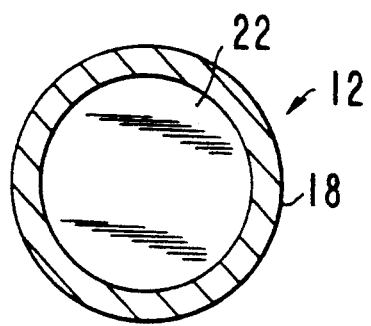
FIG. 4 is a cross-sectional view of a drilled needle butt end prior to forming the aperture into an elliptical shape.
Figure 5:
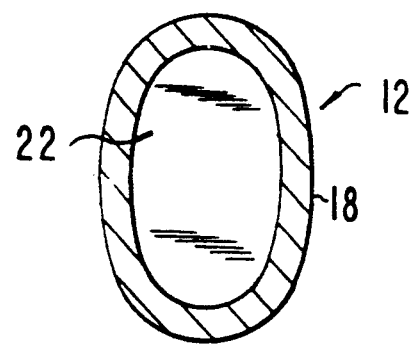
FIG. 5 is a cross-sectional view of the drilled needle butt end shown in FIG. 4 after partially compressing the butt end such that the aperture assumes an elliptical shape.
Figure 6:
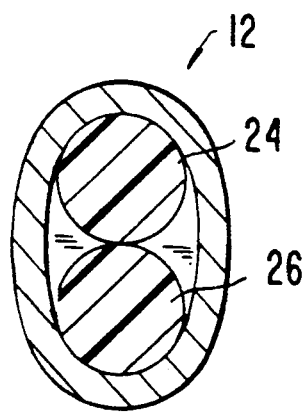
FIG. 6 is a cross-sectional view of the drilled needle butt end of FIG. 5 with the free ends of the looped suture inserted into the elliptical aperture prior to swaging.

The preferred method of attaching the flexible suture material 14 to the butt end 18 of the needle 12 is best illustrated by FIGS. 4–7. Needle 12 is initially provided with an oversized drilled aperture 22 extending axially of the butt end and having a predetermined length as shown in FIG. 3. The aperture is surrounded on all sides by the material forming the needle butt as shown in FIG. 4. Moreover, the expression "drilled aperture" contemplates a needle drilled by mechanical means, laser or the like. However, any needle having an elongated aperture as described is contemplated, regardless of how the aperture is formed in the butt end of the needle. The initial aperture is oversized with respect to the size of the flexible suture material, i.e., capable of freely receiving both free ends loosely. The butt end of the needle is first compressed inwardly using a reduced swaging pressure with an appropriate die or tool to cause the butt end 18 to assume an elliptical cross-section as shown in FIG. 5. Both free ends 24, 26 of the suture material are placed in end to end contacting relation as shown and inserted into the now elliptical aperture as shown in FIG. 6. Alternatively, a needle having a substantially elliptical opening may be provided in the first instance.

In certain applications it may be desirable to treat the ends of the suture material with a suitable tipping agent such as a cyanoacrylate. Most notable of such instances is where the suture material has a tendency to become limp or where a multifilament material is subject to a brooming effect. Thereafter, the butt end of the needle is subjected to inward force by suitable dies to cause the butt end to crimp so as to complete the attachment of the needle to the flexible suture material.

Figure 7:
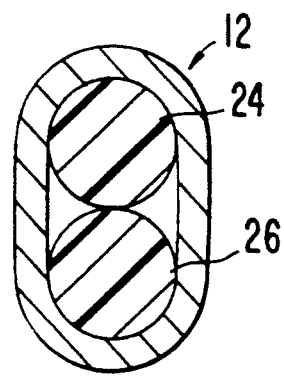
FIG. 7 is a cross-sectional view taken along lines 7-7 of FIG. 3, of the needle butt end of FIG. 6 after the needle/suture loop attachment is completed by swaging the butt end of the needle.

The attachment process may be accomplished by standard dies utilized for surgical needle/suture attachments utilizing a lap-overlap swaging die at a reduced swaging pressure, whereby the bore may be swaged under standard conditions to secure the flexible material to the needle as shown in FIG. 7. A "double hit" technique may be used whereby the needle suture attachment is accomplished by sequential hits along mutually perpendicular directions. Depending upon the intended application, any number of multiple hits may be used, rotating the direction of hit with respect to the needle 90 degrees between hits.

Alternatively, the attachment may be accomplished utilizing such apparatus as disclosed in the aforementioned commonly assigned U.S. Pat. Nos. 5,046,350 and 5,099,676. Both of the last mentioned applications are incorporated by reference herein and made a part of this disclosure. In either case, with such improved devices as disclosed in the aforementioned applications, the needle will be swaged by a single hit as disclosed in these applications.

Also, the swaging action may be carefully and precisely controlled to provide for controlled release of the needle from the suture material by predetermined forces after the suture attachment on the body tissue is completed.

The present invention combines a surgical needle with a looped suture material wherein the length of the loop is substantially greater than the length of the needle to facilitate tieing the suture material in a knot or other tie. Thus, the combination of the attachment disclosed herein and the unique relatively lengthy suture loop material form significant features of the invention. Further, any type of surgical needle is contemplated, including curved needles, straight needles, etc., of various alternative surgically approved materials.

Examples of typical combined looped devices as disclosed herein and attached by double hit techniques are as follows:

EXAMPLE 1

1. Surgical stainless steel needle
2. Needle type: half inch taper point
3. Wire size O.D. 0.062"
4. Aperture size I.D. Unswaged: 0.035–0.0365"
5. Monofilament size #1 Polypropylene 60" loop, doubled to 30" length
6. Needle elliptical aperture, major dimension 0.066"; minor dimension range: 0.038–0.042"
7. Swaging conditions: lap overlap conventional die: 0.062"
8. Long land width of die: 0.045" (range 0.040–0.060")
   —Corresponds to depth of aperture—
9. Machine pressure: 40 to 60 PSI
10. Hits required to produce minimum holding force of 2.10 kg = two to three hits, turning needle 90° after each swage.

EXAMPLE 2

1. Surgical stainless steel needle
2. Needle Type: Half inch taper point
3. Wire Size: O.D. 0.062
4. Aperture Size: I.D. Unswaged 0.040–0.0415"
5. Needle Elliptical Aperture
   Major dimension 0.070"
   Minor dimension range: 0.030–0.0365"
6. Polypropylene size #2, 60" loop doubled to 30" length
7. Swaging conditions: lap overlap conventional die 0.062"
8. Long land width of die: 0.045" (range 0.040–0.060")
   —Corresponds to length of aperture—
9. Machine pressure: 40 to 60 PSI
10. Hits required to produce minimum holding force of 2.10 kg = two to three hits, turning needle 90° after each swage.

EXAMPLE 3

1. Surgical stainless steel needle
2. Needle Type: Half inch taper point
3. Wire Size: O.D. 0.062
4. Aperture Size: I.D. Unswaged 0.040–0.0415"
5. Needle Elliptical Aperture
   Major dimension 0.070"
   Minor dimension range: 0.030–0.0365"
6. Braided Synthetic Absorbable suture size #1, 60" loop doubled to 30" length
7. Swaging conditions: lap overlap conventional die 0.062"
8. Long land width of die: 0.045" (range 0.040–0.060")
   —Corresponds to length of aperture—
9. Machine pressure: 40 to 60 PSI
10. Hits required to produce minimum holding force of 2.10 kg = two to three hits, turning needle 90° after each swage.

Preferred suture materials include absorbable or non-absorbable, natural or synthetic monofilament, multifilament or braided suture materials. Preferred suture materials include monofilament polypropylene and synthetic polymers having glycolic acid ester linkages subject to hydrolytic degradation to non-toxic, tissue compatible absorbable components including polyglycolic acid, multifilament braided sutures or the like. Other suture materials contemplated include silk, nylon, linen, cotton, polyester, stainless steel, and natural materials such as catgut.

What is claimed is:

1. In combination, a needle having a pointed end and a butt end, said butt end having an aperture extending generally axially thereof and having a substantially elliptical cross-sectional configuration for reception of needle suture material, a suture loop formed from flexible suture material, said flexible suture material having two free ends positioned in engaged adjacent relation within said substantially elliptical aperture of said needle such that the combined dimension of said free ends of suture material corresponds generally to the greater cross-sectional dimension of said aperture, said flexible suture material being of length at least about 60 inches such that said loop is about 30 inches in length to facilitate insertion of said needle and at least a portion of said flexible looped suture material into body tissue to be sutured, and looping said needle through said lop to tie said suture material with respect to body tissue, said needle being inwardly swaged at said butt end to provide predetermined inward attachment force on said free ends of said suture material sufficient to attach said suture material to said needle.

2. The looped suture device according to claim 1 wherein said needle is a surgical needle.

3. The looped suture device according to claim 2 wherein said needle has an arcuate configuration.

4. The looped suture device according to claim 3 wherein said needle is manufactured of 400 series surgical stainless steel.

5. The looped suture device according to claim 4 wherein said elongated aperture has a substantially elliptical cross-sectional configuration.

6. The looped suture device according to claim 5 wherein said flexible suture material is at least one of suture materials such as polypropylene, silk, nylon, linen, cotton, polyester, stainless steel, natural materials such as catgut, and synthetic polymers having glycolic acid ester linkages subject to hydrolytic degradation to non-toxic, tissue compatible absorbable components, including polyglycolic acid.

7. The looped suture device according to claim 6 wherein said butt end of said pointed needle is inwardly swaged in at least two directions to provide inward forces directed at said flexible suture material to attach said suture material to said needle.

8. The looped suture device according to claim 7 wherein said swaged attachment at said butt end of said needle is controlled to provide predetermined pull-out forces of said flexible suture material with respect to said needle.

9. The looped suture device according to claim 8 wherein said pull out forces average approximately 2.10 kilogram-force.

10. The looped suture device according to claim 1 wherein said flexible suture material has a generally circular cross-sectional configuration.

11. A method of manufacturing a looped suture device which comprises:
   a) providing a surgical needle having a pointed end and a butt end, said butt end having an elongated aperture extending axially thereof and being of predetermined length;
   b) providing a flexible suture material and looping said suture material such that the two free ends thereof are in adjacent engaged end to end relation, said flexible suture material being of sufficient length to facilitate insertion of said needle and at least a portion of said flexible material into body tissue to be sutured, and looping said needle through said loop to tie said suture material with respect to body tissue;
   c) deforming said butt end of said needle such that said aperture assumes a substantially elliptical cross-sectional shape having a major dimension greater than a minor dimension substantially perpendicular to said major dimension, said aperture of said needle being dimensioned sufficient to receive a predetermined length of said free end portions of said flexible suture material while maintaining said free end portions in said end to end relation;
   d) positioning a pair of dies about said butt end of said needle and;
   e) applying at least one inwardly directed force to said dies and thereby to said butt end of said needle to cause said needle material to become inwardly swaged sufficient to provide inward predetermined attachment force on said suture material.

12. The method according to claim 11 wherein said flexible suture material has a generally circular cross-sectional configuration.

13. The method according to claim 11 further comprising treating the free end portions of said flexible suture material with a tipping agent prior to positioning said free end portions within said aperture of said needle.

14. The method according to claim 13 wherein said tipping agent is a cyanoacrylate.

15. The method according to claim 14 further comprising providing at least a second inwardly directed force on said butt end of said needle in a direction generally perpendicular to said first provided force to thereby cause said needle material to become further swaged to provide predetermined attachment force on said flexible suture material.

16. A method of manufacturing a looped suture device which comprises:
   a) providing a surgical needle having a pointed end and a butt end, said butt end having an aperture extending axially thereof and of predetermined length;
   b) providing a flexible suture material and looping said suture material such that the two free ends thereof are in adjacent engaged end to end relation;
   c) deforming said butt end such that said aperture of said needle assumes a cross-sectional shape having a major dimension greater than a minor dimension substantially perpendicular to said major dimension, said aperture of said needle being dimensioned sufficient to receive a predetermined length of said free end portions of said flexible suture material while maintaining said free end portions in said end to end relation;
   d) positioning a pair of dies about said butt end of said needle, each die having a generally arcuate undulating surface portion facing said butt end and including concave portions; and
   e) applying inward force to said dies to cause said dies to strike said needle butt end to transmit inward crimping forces thereto so as to attach said flexible suture material to said needle while permitting deformed material of said needle butt end to collect within said concave portions so as to avoid distortion of said butt end.

17. The method according to claim 16 wherein said flexible suture material has a generally circular cross-sectional configuration.

18. A method of manufacturing a looped suture device which comprises:
   a) providing a surgical needle having a pointed end and a butt end, said butt end having an aperture extending axially thereof and of predetermined length;
   b) providing a flexible suture material and looping said suture material such that the two free ends thereof are in adjacent engaged end to end relation;
   c) deforming said butt end such that said aperture of said needle assumes a cross-sectional shape having a major dimension greater than a minor dimension substantially perpendicular to said major dimension, said aperture of said needle being dimensioned sufficient to receive a predetermined length of said free end portions of said flexible suture material while maintaining said free end portions in said end to end relation;
   d) positioning a pair of dies about said butt end of said needle, each die having a pair of inner arcuate surface portions spaced apart from each other to provide a material relief zone; and
   e) applying inward force to said dies sufficient to cause crimping of said needle butt end so as to attach said flexible suture material to said needle while permitting portions of material forming part of said butt end to be deformed and to collect within relief zones between said pairs of arcuate surface portions.

19. The method according to claim 18 wherein said flexible suture material has a generally circular cross-sectional configuration.

20. A method of manufacturing a looped suture device which comprises:
 a) providing a surgical needle having a pointed end and a butt end, said butt end having an aperture extending axially thereof and of predetermined length;
 b) providing a flexible suture material and looping said suture material such that the two free ends thereof are in adjacent engaged end to end relation, said flexible suture material being of sufficient length to facilitate insertion of said needle and at least a portion of said flexible suture material into body tissue to be sutured, and looping said needle through said loop to tie said suture material with respect to body tissue;
 c) deforming said butt end such that said aperture of said needle assembly assumes a substantially elliptical cross-sectional shape;
 d) inserting a predetermined length of said free end portions of said suture material into said substantially elliptical aperture while maintaining said free end portions in end to end relation;
 e) providing a first inwardly directed force in a first direction; and
 f) providing a second inwardly directed force in a second direction different from said first direction to swage said butt end to said suture.

21. The method of claim 20 wherein said first and second directions are substantially perpendicular to each other.

22. A method of suturing body tissue with a looped suture device having a needle having a pointed end and a butt end, said butt end having an aperture extending generally axially thereof and having a cross-sectional dimension greater in a first direction than the cross-sectional dimension substantially perpendicular to said first direction, a loop formed from a flexible suture material and having both free ends positioned within said aperture and attached to said needle, comprising inserting said needle into the body tissue until at least a portion of said suture material penetrates the body tissue, substantially reversing the direction of said needle and inserting said needle through said looped suture material.

23. A method of manufacturing a looped suture device which comprises:
 a) providing a surgical needle having a pointed end and a butt end, said butt end having an elongated aperture extending generally axially thereof and said aperture having a cross-section dimension greater in a first direction than the cross-dimension substantially perpendicular to said first direction;
 b) providing a flexible suture material and looping said suture material such that the two free ends thereof are in adjacent engaged end to end relation, said flexible suture material being of sufficient length at least about 60 inches such that the length of the resilient loop is at least about 30 inches to facilitate insertion of said needle and at least a portion of said flexible suture material into body tissue to be sutured, and looping said needle through said loop to tie said suture material with respect to body tissue;
 c) inserting a predetermined length of said free end portions of said suture material into said elongated aperture while maintaining said free end portions in end to end relation; and
 d) providing at least one inwardly directed force on said butt end of said needle to cause said needle material to become inwardly swaged sufficient to provide inward predetermined attachment force on said suture material.

24. A method of repairing body tissue, comprising:
 a) providing a looped suture device having a pointed end and a butt end, said butt end having an aperture extending generally axially thereof and having a cross-sectional dimension greater in a first direction than the cross-section dimension substantially perpendicular to said first direction, a loop formed from a flexible suture material and having both free ends positioned within said aperture and attached to said needle, said flexible suture material being of sufficient length to facilitate looping said needle through said loop to tie said suture material with respect to body tissue;
 b) inserting said needle into the body tissue at a location and in direction to effect a repair;
 c) passing said needle and a substantial portion of said flexible suture material through the body tissue;
 d) inserting said needle through said looped portion of suture material to tie said suture material with respect to said looped portion and the body tissue.

25. A method of manufacturing a looped suture device which comprises:
 a) providing a surgical needle having a pointed end and a butt end, said butt end having an aperture extending axially thereof and being of predetermined length;
 b) providing a flexible suture material and having a generally circular cross-sectional configuration;
 c) treating the free end portions of said flexible suture material with a tipping agent;
 d) looping said suture material such that the two free ends thereof are in adjacent engaged end to end relation, said flexible suture material being of sufficient length to facilitate insertion of said needle and at least a portion of said flexible material into body tissue to be sutured, and looping said needle through said loop to tie said suture material with respect to body tissue;
 e) deforming said butt end of said needle such that said aperture assumes a substantially elliptical cross-sectional shape having a major dimension greater than a minor dimension substantially perpendicular to said major dimension, said aperture of said needle being dimensioned sufficient to receive a predetermined length of said free end portions of said flexible suture material while maintaining said free end portions in said end to end relation; and
 f) providing at least one inwardly directed force to said dies and thereby on said butt end of said needle to cause said needle to become inwardly swaged sufficient to provide inward predetermined attachment force on said suture material.

26. The method according to claim 25 wherein said tipping agent is a cyanoacrylate.

* * * * *